(12) United States Patent
Garrigue et al.

(10) Patent No.: US 9,682,147 B2
(45) Date of Patent: Jun. 20, 2017

(54) SELF-PRESERVED OIL DISPERSIONS COMPRISING BORIC ACID

(71) Applicant: SANTEN SAS, Evry (FR)

(72) Inventors: Jean-Sébastien Garrigue, Verrières le Buisson (FR); Frédéric Lallemand, Fresnes (FR); Betty Philips, Antony (FR)

(73) Assignee: SANTEN SAS, Evry (FR)

( * ) Notice: Subject to any disclaimer, the term of this patent is extended or adjusted under 35 U.S.C. 154(b) by 0 days.

(21) Appl. No.: 14/380,655

(22) PCT Filed: Feb. 22, 2013

(86) PCT No.: PCT/EP2013/053556
§ 371 (c)(1),
(2) Date: Aug. 22, 2014

(87) PCT Pub. No.: WO2013/124415
PCT Pub. Date: Aug. 29, 2013

(65) Prior Publication Data
US 2015/0025020 A1    Jan. 22, 2015

Related U.S. Application Data

(60) Provisional application No. 61/602,369, filed on Feb. 23, 2012.

(30) Foreign Application Priority Data

Feb. 23, 2012    (EP) .................................... 12156652

(51) Int. Cl.
| | | |
|---|---|---|
| A61K 47/02 | (2006.01) |
| A61K 9/107 | (2006.01) |
| A61K 31/5575 | (2006.01) |
| A61K 47/10 | (2017.01) |
| A61K 31/436 | (2006.01) |
| A61K 47/18 | (2017.01) |
| A61K 47/26 | (2006.01) |
| A61K 47/44 | (2017.01) |
| A61K 38/13 | (2006.01) |
| A61K 31/573 | (2006.01) |
| A61K 9/00 | (2006.01) |
| A61K 47/34 | (2017.01) |
| A61K 33/22 | (2006.01) |

(52) U.S. Cl.
CPC ............ *A61K 47/02* (2013.01); *A61K 9/0048* (2013.01); *A61K 9/107* (2013.01); *A61K 9/1075* (2013.01); *A61K 31/436* (2013.01); *A61K 31/5575* (2013.01); *A61K 31/573* (2013.01); *A61K 33/22* (2013.01); *A61K 38/13* (2013.01); *A61K 47/10* (2013.01); *A61K 47/186* (2013.01); *A61K 47/26* (2013.01); *A61K 47/34* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,597,559 A | 1/1997 | Olejnik et al. | |
| 6,492,361 B1 | 12/2002 | Muller et al. | |
| 6,528,070 B1 * | 3/2003 | Bratescu ................. | A61K 8/06 424/401 |
| 2003/0118528 A1 * | 6/2003 | Walters ................ | A61K 9/0014 424/59 |
| 2004/0191332 A1 | 9/2004 | Chang et al. | |
| 2006/0233739 A1 | 10/2006 | Thornfeldt et al. | |
| 2008/0089953 A1 | 4/2008 | Chowhan et al. | |
| 2010/0137252 A1 | 6/2010 | Matsumura et al. | |
| 2010/0137432 A1 * | 6/2010 | Khopade et al. ............. | 514/530 |
| 2011/0118349 A1 | 5/2011 | Garrigue et al. | |
| 2011/0136912 A1 | 6/2011 | Ketelson et al. | |

FOREIGN PATENT DOCUMENTS

| | | |
|---|---|---|
| EP | 0861658 A1 | 9/1998 |
| JP | 2006521362 A | 9/2006 |
| WO | 98/06381 | 2/1998 |
| WO | 2004087098 A2 | 10/2004 |
| WO | 2008036847 A2 | 3/2008 |
| WO | 2008036855 A2 | 3/2008 |
| WO | 2008042619 A2 | 4/2008 |
| WO | 2010064636 A1 | 6/2010 |

OTHER PUBLICATIONS

Anonymous, "Eucerin Original Moisturizing Lotion", Internet Article, Available at URL: http://www.ewg.org/skindeep/product/3030/eucerin_original_moisterizing_Lotion/ [Retrieved Jun. 28, 2012], 2007, 1-1.
European Patent Office; PCT International Search Report mailed Apr. 23, 2013; PCT/EP2013/053556; 3 pages.
Gorbet M.B., Tanti N.C., Jones L. and Sheardown H., Molecular Vision, 2010, 16, 272-282.
Houlsby R.D., Ghajar M. and Chavez G., Antimicrobial Agent and Chemotherapy, 1986, 29(5), 803-806.
Sznitowska M., Janicki S., Dabrowska E.A. and Gajewska M., Eur. J. Pharm. Sci., 2002, 15(5), 489-95.
Tanti N.C., Jones L. and Gorbet M.B., Optometry and Vision Science, 2011, 88(4), 483-492.

(Continued)

*Primary Examiner* — Robert A Wax
*Assistant Examiner* — Randeep Singh
(74) *Attorney, Agent, or Firm* — Young & Thompson

(57) ABSTRACT

The present invention relates to a self-preserved oil dispersion. Especially, the present invention relates to a self-preserved oil dispersion including a dispersed oil phase, an aqueous phase and at least one surfactant, wherein said oil dispersion comprises boric acid in an amount ranging from 0.005% to 0.075% in weight of the total weight of the oil dispersion, said amount of boric acid being a preservative effective amount so that the oil dispersion has a preservative activity.

14 Claims, No Drawings

(56) References Cited

OTHER PUBLICATIONS

Teranishi S., Chikama T.-I., Kimura K. and Nishida T., XIX Biennial Meeting of the International Society for Eye Research, Jul. 18-23, 2010, Montreal, Canada.
Teejel Gel, leaflet information, Oct. 2, 1979.
"Handbook of preservatives", Compiled by Ash M. and Ash I., 2004, p. 686, Synapse Information Resources.
Daull P., Lallemand F. and Garrigue J.S., "Benefits of cetalkonium chloride cationic oil-in-water nanoemulsions for topical ophthalmic drug delivery", Journal of pharmacy and pharmacology, vol. 66, No. 4, 2014, pp. 531-541.
The Merck Index, "Entry 2034. Cetrimonium bromide", 2001, 2 pages.

* cited by examiner

SELF-PRESERVED OIL DISPERSIONS COMPRISING BORIC ACID

This application is a national stage application under 35 U.S.C. §371 of International Application No. PCT/EP2013/053556, filed Feb. 22, 2013, entitled "SELF-PRESERVED OIL DISPERSIONS COMPRISING BORIC," which claims priority to European Patent Application No. 12156652.5, filed Feb. 23, 2012, and to U.S. Provisional Patent Application No. 61/602,369, filed Feb. 23, 2012.

FIELD OF INVENTION

The present invention relates to a self-preserved oil dispersion. Especially, the invention relates to an ophthalmic oil dispersion formulated to have sufficient preservative activity to meet preservation efficacy requirement of European and US pharmacopeias or equivalent guidelines in other countries without including conventional preservative agents. Especially, the present invention provides an ophthalmic oil dispersion comprising a low amount of boric acid sufficient to make it preserved while being well tolerated on the eye and not containing conventional preservative agents.

BACKGROUND OF INVENTION

Many pharmaceutical compositions are manufactured under sterile conditions.

In the case of "multi-dose" packaging of sterile compositions, it is required that the composition remains sterile after opening the packaging and during period of use. This is especially the case for ophthalmic eye drops which are applied topically directly on the surface of the eye. This eye drop should not, in any way, become a vehicle susceptible of carrying bacterial or fungal contamination into the eye. Consequently, after opening a multi-dose packaging, ophthalmic composition should remain sterile during the period of use i.e. about 15 days in most cases, and should therefore have sufficient preservative activity to comply with the preservation efficacy requirements of the US pharmacopeia (USP) and European pharmacopeia (Ph. Eur.) or analogous guidelines in other countries. A composition with a preservative activity should be understood, in the meaning of the present invention, as a composition in which there is few, if any, microbial or fungal proliferation and which satisfies the preservation efficacy requirements of pharmacopeias. In the meaning of this invention, a preservative activity is related to keeping the composition safe, sterile and clean, and is not related with any therapeutic effect. On the contrary, the term "antimicrobial activity" refers to a therapeutic effect of a composition when applied on the eye of a patient, in order to avoid or to eliminate the presence of germs in the eye.

One solution to prevent contamination of a composition after opening of a multi-dose container is to use a specific packaging system, including for example specific filters placed on the opening. This solution presents the drawback of being very expensive and not accepted by some and any health authorities.

Another solution to maintain a composition sterile after opening the packaging is to include preservative agents in the formulation, generally composed of cetrimide, cetylpyridinium chloride, polyquaternium, benzalkonium chloride, benzethonium chloride, benzododecinium or other classes of preservatives such as chlorobutanol, mercurial preservatives and parabens. However, these preservatives are known to be irritant and not well tolerated by patients, especially when used chronically. Consequently, in order to minimize harmful effects, there is a need to use less toxic preservatives and/or to use preservative agents at the lowest possible concentrations (i.e. the minimum amount required to obtain a preservative activity).

Less toxic preservatives may be for example purite, oxychloro complex or sodium perborate, that act by releasing oxygen in the environment of the microorganisms. However, these products present the drawback to be heat sensitive and therefore are not compatible with ophthalmic compositions that should be sterilized by heat or able to be kept in hot climate.

Therefore, there is also a need for new preserved ophthalmic compositions that do not induce adverse effect for the eyes linked to the presence of preservative agents, that may be easily sterilized and that are not heat sensitive.

Compositions that do not contain a preservative effective amount of a conventional preservative agents but are still preserved from microbial and/or fungal contaminations have been referred to in the art as being "preservative free" or "self-preserved" compositions (see for example U.S. Pat. No. 5,597,559 or U.S. Pat. No. 6,492,361).

The concept of self-preserved compositions was developed in prior patent applications, for example WO2008042619, WO200836847, WO200836855. Aqueous solutions described in these patent applications do not comprise conventional preservative agents. They are based on the use of zinc ions together with either (i) a limited concentration of anionic species or (ii) complexes of borate plus excipients (such as polyol or amino alcohol).

The use of boric acid to preserve aqueous solutions is described in specific concentrations only; indeed, boric acid concentrations to be used in order to obtain an antibacterial effect in a solution are quite high, i.e. more than 1.2% w/w. It was reported that a solution comprising 1.2% w/w of borate had some antimicrobial activity but that this concentration was not sufficient to meet the criteria for antimicrobial effectiveness given by USP (Houlsby R. D., Ghajar M. and Chavez G., *Antimicrobial Agent and Chemotherapy*, 1986, 29(5), 803-806).

In self-preserved solutions described in patent applications WO2008042619, WO200836847, WO200836855, the use of zinc ions or of excipients allows reducing the concentration of borate in the solution to obtain effective preservative activity in the meaning of USP: borate is used there in amounts ranging from 0.15% to 1% in weight of the total weight of the composition.

Patent application US2008089953 describes a composition containing tobramycin, an antibiotic, with a complex of borate and glycerol to enhance the preservative effect of tobramycin itself. A high quantity of borate (1%) is necessary to obtain a fully self-preserved composition.

Therefore, it was well admitted that boric acid is a rather weak preservative agent and that elevated concentrations of boric acid have to be used to obtain preserved compositions.

Literature reports cases of toxicity induced by boric acid on corneal cells.

Teranishi et al. showed that the concentration of 0.1% boric acid to be safe while 0.5% to 1% are toxic to corneal and epithelial cells (Teranishi S., Chikama T.-I., Kimura K. and Nishida T., *XIX Biennial Meeting of the Internatioanl Society for Eye Research*, Jul. 18-23, 2010, Montreal, Canada).

It was also reported that when boric acid is used in cleaning contact lenses solutions a strong corneal cytotoxicity can be observed (Tanti N. C., Jones L. and Gorbet M. B., *Optometry and Vision Science*, 2011, 88(4), 483-492;

Gorbet M. B., Tanti N. C., Jones L. and Sheardown H., *Molecular Vision,* 2010, 16, 272-282).

Therefore, it is well admitted in the art that the use of boric acid in ophthalmic compositions may result in corneal toxicity after topical application when highly concentrated.

In the field of oil dispersions, especially ophthalmic oil-in-water emulsions, preservative agents commercially used are generally the same as the conventional ones used in ophthalmic solutions. Therefore, similar issues of irritation and side-effects are encountered.

As emulsions are very sensitive systems, especially relative to stability concerns, developing new preservative systems is very challenging. Moreover, it has been demonstrated that numerous commonly used preservative agents are neutralized in oil-in-water emulsions by inclusion in the oily phase (Sznitowska M., Janicki S., Dabrowska E. A. and Gajewska M., *Eur. J. Pharm. Sci.,* 2002, 15(5), 489-95). Indeed, Sznitowska et al. investigated the distribution of different preservative agents between water phase and oily phase. They found that an important part of these preservative agents, even water-soluble ones, was found to be in oily phase. As a result, preservative efficacy was reduced relative to what may be expected with the total concentration of preservative used.

Surprisingly, the Applicant found that oil dispersions could be preserved and meet preservation efficacy requirements of pharmacopeias by using a very small amount of boric acid, said dispersions not encompassing any other preservative agent. Such dispersions were found to be safe for the eyes and not toxic to corneal cells. Without willing to be linked by a theory, the Applicant believes that it may be the fact that the eye drop composition is a dispersion, and not a solution, that may impact the effect of boric acid: amounts of boric acid used in the dispersions of the present invention are lower than the amounts described in the prior art to preserve solutions.

The Applicant found that (1) a solution encompassing a low concentration of boric acid, in absence of any other preservation system or agent, has no preservative activity and (2) on the contrary a dispersion of the invention encompassing a low concentration of boric acid, in absence of any other preservation system or agent, has a preservative activity.

This invention was quite surprising, as in the knowledge of the Applicant, nothing in the prior art disclose or suggest that using low amounts, i.e. non-toxic amounts of boric acid could, in absence of any other conventional preservative, lead to a self-preserved dispersion. Especially, the use of boric acid in ophthalmic oil-in-water emulsion in concentrations described therein is not disclosed or suggested by the prior art for manufacturing self-preserved emulsions or for manufacturing emulsions having a preservative activity.

Without willing to be linked by any theory, this unexpected phenomenon could be explained by a synergy between the oily phase of the oil dispersion and boric acid, said synergy resulting in a preservative activity. For this reason, boric acid will be referred to as a "preservation promoter" in the following description.

The Applicant also found that when the oil dispersion is positively charged, boric acid seems to have an even much stronger effect so that a lower concentration of boric acid is required for a cationic oil dispersion with comparison to a non-ionic oil dispersion.

Therefore, the present invention presents the advantage of providing a preserved oil dispersion comprising a low amount of boric acid, being free of conventional preservative agents and being of safe-use on the eye.

SUMMARY

This invention thus relates to a self-preserved oil dispersion including a dispersed oil phase, an aqueous phase and at least one surfactant, wherein said oil dispersion comprises boric acid in an amount ranging from 0.005% to 0.075% in weight of the total weight of the oil dispersion, said amount of boric acid being a preservative effective amount so that the oil dispersion has a preservative activity.

According to one embodiment, the oil dispersion of the invention has a sufficient preservative activity to comply with USP and/or Ph. Eur. preservative efficacy requirements, said pharmacopeias being herein incorporated by reference. In an embodiment, compliance with USP and/or Ph. Eur. means that the dispersion shall have sufficient preservative activity to inhibit the growth and decrease the population of *Escherichia coli, Pseudomonas aeruginosa, Staphylococcus aureus, Candida albicans, Aspergillus niger* or *Aspergillus.*

According to one embodiment, the oil dispersion of the invention is an oil-in-water emulsion.

According to one embodiment, the amount of boric acid in the oil dispersion of the invention ranges from 0.008 to 0.05%, preferably from 0.01 to 0.05%, more preferably from 0.01 to 0.02% w/w.

According to one embodiment, boric acid, in the meaning of this invention, include any form of boric acid or salt thereof, especially sodium borate, sodium metaborate, calcium borate, borax, tricopper diborate, trioleyl borate, lithium borate, tris(trimethylsilyl) borate, ethyl borate, potassium tetrafluoroborate, disodium dihydrogen borate, manganese borate, oleyl borate, tripentyl borate, tributyl borate, trimethyl borate, tridodecyl borate, triazanium borate or a mixture thereof.

According to one embodiment, the oil phase comprises an oil selected from mineral oil such as petrolatum or liquid paraffin; medium chain triglycerides (MCT); triglycerides oils, vegetable oils such as castor oil, corn oil, olive oil, soybean oil, sesame oil, cotton seed oil, sweet almond oil or any suitable vegetable oil; fatty acid, isopropyl myristate, oily fatty alcohols, esters of sorbitol and fatty acids, oily sucrose esters or a mixture thereof.

According to one embodiment, the oil dispersion of the invention comprises a cationic surfactant.

According to one embodiment, the cationic surfactant is selected from cetalkonium chloride (CKC), benzethonium chloride, cetrimide, cationic lipids, oleylamine, stearylamine, DOTAP (N-[1-(2,3-dioleoyloxy) propyl]-N,N,N trimethylammonium) chloride, DOPE (dioleoyl phosphatidylethanolamine), poly(ethylenimine) (PEI), poly-L-lysine (PLL) or a mixture thereof.

According to one embodiment, the oil dispersion of the invention comprises a non-ionic surfactant.

According to one embodiment, the non-ionic surfactant is selected from tyloxapol, poloxamer such as poloxamer 282 or poloxamer 188 or Pluronic F-68LF or Lutrol F68, polysorbate such as polysorbate 20 or polysorbate 80, solutol, polyoxyethylene fatty acid esters such as Emulphor, polyoxyethylene alkyl ethers, polyoxyethylene castor oil derivatives such as Cremophor EL or Cremophor RH, polyoxyethylene sorbitan fatty acid esters, polyoxyethylene stearates, sodium lauryl sulfate, sorbitan esters, vitamin E derivatives such as vitamin E-tocopheryl polyethylene glycol succinate or a mixture thereof.

According to one embodiment, the oil dispersion of the invention further comprises a therapeutically active agent.

According to one embodiment, the therapeutically active agent is selected from antiallergenics such as sodium cromoglycate, antazoline, methapyriline, chlorpheniramine, cetirizine, olapatadine, ketotifen, azelastine, epinastine, emedastine, levocabastive, terfenadine, astemizole and loratadine, pyrilamine or prophenpyridamine; synthetic glucocorticoids and mineralocorticoids and more generally hormones forms derivating from the cholesterol metabolism (progesterone, estrogens, androgenic hormones such as testosterone DHEA and their derivatives); anti-inflammatories such as cortisone, hydrocortisone, hydrocortisone acetate, dexamethasone, dexamethasone 21-phosphate, fluorocinolone, medrysone, prednisone, methylprednisone, prednisolone acetate, fluoromethalone, triamcinolone, betamethasone, loteprednol, flumethasone, mometasone, danazol, beclomethasone, difluprednate and triamcinolone acetonide and their derivatives; non-steroidal anti-inflammatories such as salicylate, indomethacin, ibuprofen, diclofenac, flurbiprofen, 2-arylpropionic acids, N-arylanthranilic acids, oxicams, sulphonanilides, pyrazolidines derivatives, arylalkanoic acids, 3-benzolphenylacetic acids and derivatives, piroxicam and COX2 inhibitors such as rofecoxib, diclofenac, nimesulide, nepafenac; antineoplastics such as carmustine, cisplatin, mitomycin and fluorouracil; immunological drugs such as vaccines and immune stimulants; insulin, calcitonin, parathyroid hormone and peptide and vasopressin hypothalamus releasing factor; beta adrenergic blockers such as timolol maleate, levobunolol HCl and betaxolol HCl, timolol-base, betaxolol, atenolol, befundol, metipranolol, forskolin, cartrolol, epinephrine, dipivalyl, oxonolol, acetazolamide-base and methazolamide; cytokines, interleukins, prostaglandins (also antiprostaglandins, and prostaglandin precursors) such as latanoprost, bimatoprost, tafluprost or travoprost, and growth factors (growth factors such as epidermal growth factor, fibroblast growth factor, platelet derived growth factor, transforming growth factor beta, ciliary neurotrophic growth factor, glial derived neurotrophic factor, NGF, EPO, PlGF); anti-angiogenic compounds such as VEGF inhibitors, VEGF soluble receptors, VEGF-traps, VEGF-antibodies, VEGF-traps, anti VEGF-siRNA; antibodies or antibodies fragments, oligoaptamers, aptamers and gene fragments (oligonucleotides, plasmids, ribozymes, small interference RNA, nucleic acid fragments, peptides, antisense sequences); immunomodulators such as natural or synthetic cyclosporines, endoxan, sirolimus, tacrolimus, thalidomide, tamoxifene; secretagogues such as pilocarpine or celameline; mucin secretagogues such as 15(S)-HETE, ecabet or diquafosol; antithrombolytic and vasodilator agents such as rtPA, urokinase, plasmin, nitric oxide donors; androgen mimetics, flaxseed oil supplements, agonists of adenosine A3 receptor, squalene; antioxidants such as lutein, vitamins, especially vitamin A; inhibitors of carbonic anhydrase such as brinzolamide, dorzolamide, acetazolamide, methazolamide, dichlorophenamide; sympathomimetics such as brimonidine, apraclonidine, dipivefrine, epinephrine; parasympathomimetics such as pilocarpine; cholinesterase inhibitors such as physostigmine, echothiophate; antivirals, such as idoxuridine, trifluorotymidine, acyclovir, valaciclovir, ganciclovir, cidofovir and interferon; antibiotics such as aminoglycosides, carbacephem, carbapenems, cephalosporins, glycopeptides, penicillins, polypeptides, quinolones, sulfonamides, tetracyclines, chlortetracycline, bacitracin, neomycin, polymyxin, gramicidin, cephalexin, oxytetracycline, chloramphenicol, kanamycin, rifampicin, tobramycin, gentamycin, ciprofloxacin, aminosides, erythromycin, ceftazidime, vancomycine, imipeneme; antifungals such as polyene antibiotics, azole derivatives, imidazole, triazole, allylamines, amphotericin B and miconazole; antibacterials such as sulfonamides, sulfadiazine, sulfacetamide, sulfamethizole and sulfisoxazole, nitrofurazone and sodium propionate; and/or their derivatives; and/or their prodrugs; and/or their precursors; and/or acceptable salts thereof; alone or in combination.

According to one embodiment, the oil dispersion of the invention is for use in the treatment of an eye disease or eye condition.

The present invention also relates to a process of manufacturing of the oil dispersion of the invention, comprising the steps of emulsifying and mixing the aqueous phase and the oil phase with surfactant.

The present invention also relates to a multi-dose container including the oil dispersion of the invention. The present invention also relates to a mono-dose container including the oil dispersion of the invention.

The present invention also relates to boric acid in an oil dispersion, in an amount ranging from 0.005% to 0.075% in weight of the total weight of the oil dispersion, for use as a preservation promoter.

DEFINITIONS

In the present invention, the following terms have the following meanings:

"a composition with a preservative activity" or "a preserved composition" refers to a composition that is protected from microbial and/or fungal contamination and/or proliferation, or in which there is few, if any, microbial and/or fungal proliferation or that satisfies the preservation efficacy requirements of pharmacopeias.

"a composition with an antimicrobial activity" or "an antimicrobial composition" refers to a composition that has a therapeutic antimicrobial effect when applied on a patient.

"preservative agent" refers to a compound that provides preservative activity to the composition in which it is encompassed, when used in sufficient amount.

"conventional preservative agents" refers to preservative agents that are commonly used to prevent microbial and/or fungal proliferation, such as for example benzalkonium chloride; polyquaternium; cetrimide; benzethonium chloride; cetylpyridinium chloride; chlorite or hydrogen peroxide, methylchloroisothiazolinone, methylisothiazolinone.

"sterile composition" refers to a composition that does not present microbial and/or fungal contamination in the meaning defined in pharmacopeias.

"self-preserved composition" refers to a composition that does not contain a conventional preservative agents but is still preserved.

"a preservative effective amount" refers to an amount of a component, such as for example boric acid, that confers a preservative activity to the composition in which it is encompassed.

"oil dispersion" refers to composition comprising two non-miscible phases, with the dispersed phase possibly being liquid, solid or gas, Example of solids are nanoparticles or nanocapsules. Examples of liquids are droplets or liposomes. Examples of gas are foams. Preferred oil dispersion of the invention includes an oil phase, an aqueous phase and a surfactant that have been mixed to disperse the oil phase in the aqueous phase, the dispersion being stabilized by the surfactant. Examples of oil dispersions according to the invention are emulsions, dispersions or foam. In an embodiment, the oil dispersion is an oil-in-water emulsion. In another embodiment, the oil dispersion is a dispersion of nanoparticles, liposome or nanocapsules in an aqueous phase.

"preservation promoter" refers to a compound investing a preservative activity in an oil dispersion, where it is present in an amount that has no preservative effect in a corresponding solution containing same ingredients as the oil dispersion, except oil.

According to this invention, if not otherwise stated, concentration of the ingredients are given as "%", meaning weight of ingredient in hundred weight units of the total oil dispersion ("w/w").

DETAILED DESCRIPTION

This invention relates to an oil dispersion comprising a preservative effective amount less than 0.075% w/w of boric acid, said dispersion being self-preserved.

According to one embodiment, the oil dispersion of the invention inhibits the growth of microorganisms listed in the European and US pharmacopeias (Ph. Eur. and USP) in the oil dispersion. According to a preferred embodiment, the oil dispersion of the invention inhibits the growth of microorganisms listed in the Ph. Eur. and USP in the oil dispersion during a period ranging from 15 to 60 days, preferably from 20 to 30 days, more preferably during 28 days after opening of the container. Consequently, the preservative activity of the oil dispersion in use ranges from 15 to 60 days, preferably from 20 to 30 days, more preferably during 28 days.

According to one embodiment, the oil dispersion of the invention inhibits the growth of *Escherichia coli*, *Pseudomonas aeruginosa, Staphylococcus aureus, Candida albicans, Aspergillus niger* or *Aspergillus brasiliensis* in the oil dispersion.

According to one embodiment, the oil dispersion of the invention decreases the total number of *Escherichia coli, Pseudomonas aeruginosa, Staphylococcus aureus, Candida albicans, Aspergillus brasiliensis* or *Aspergillus niger* in the oil dispersion. In this embodiment, the decrease of the total number of microorganisms is preferably of at least two log units within a period of 14 days.

According to one embodiment, the oil dispersion of the invention is an emulsion, preferably an oil-in-water emulsion. According to one embodiment the emulsion may be non-ionic, cationic or anionic, preferably cationic. By cationic oil-in-water emulsion is understood an oil-in-water emulsion having a positive zeta potential. The zeta potential of a composition may be determined through the measure of the electrophoretic mobility of said composition.

In one embodiment, the oil dispersion of the invention is an emulsion including oil droplets having an average size of about 0.1 to 100 µm, preferably 100 to 500 nm, more preferably 150 to 300 nm.

According to one embodiment, the oil dispersion of the invention is not an aqueous suspension.

According to one embodiment, the oil dispersion of the present invention comprises boric acid in an amount ranging from 0.005 to 0.075%, preferably from 0.008 to 0.05%, more preferably from 0.01 to 0.05%, more preferably from 0.01 to 0.03%, more preferably from 0.02 to 0.03% in weight of the total weight of the oil dispersion.

According to one embodiment, boric acid may be in the form of boric acid or salt thereof, especially sodium borate, sodium metaborate, calcium borate, borax, tricopper diborate, trioleyl borate, lithium borate, tris(trimethylsilyl) borate, ethyl borate, potassium tetrafluoroborate, disodium dihydrogen borate, manganese borate, oleyl borate, tripentyl borate, tributyl borate, trimethyl borate, tridodecyl borate, triazanium borate or a mixture thereof.

According to one embodiment, the oil dispersion comprises free boric acid, i.e. not under the form of a salt thereof. According to one embodiment, the oil dispersion comprises free boric acid in an amount ranging from 0.005 to 0.075%, preferably from 0.01 to 0.075%, more preferably from 0.02 to 0.075%, more preferably from 0.02 to 0.05%.

According to another embodiment, the oil dispersion comprises a salt of boric acid or a derivative thereof, preferably borax or tricopper diborate. According to one embodiment, the oil dispersion comprises borax or tricopper diborate in an amount ranging from 0.005 to 0.075%, preferably from 0.01 to 0.075%, more preferably from 0.02 to 0.05%.

According to one embodiment, the oil of the oil dispersion of the invention comprises mineral oil such as petrolatum or liquid paraffin; heavy or light mineral oil or a mixture of both, medium chain triglycerides (MCT); triglycerides oils, vegetable oils such as castor oil, corn oil, olive oil, soybean oil, sesame oil, cotton seed oil, sweet almond oil or any suitable vegetable oil; fatty acid, isopropyl myristate, oily fatty alcohols, esters of sorbitol and fatty acids, oily sucrose esters or a mixture thereof. Preferably said oil comprises mineral oil or MCT. In one embodiment, mineral oil comprises light mineral oil and heavy mineral oil, preferably mineral oil comprises 50% of light mineral oil and 50% heavy mineral oil, in weight of the total weight of mineral oil. In one embodiment, the oil dispersion of the invention does not contain castor oil. Preferably, the oil dispersion of the invention comprises an amount of oil ranging from 0.5% to 5%, preferably from 1% to 5%, more preferably from 1% to 2% w/w.

According to one embodiment, the oil dispersion of the invention comprises a surfactant. The surfactant may be a non-ionic surfactant, an anionic surfactant, a cationic surfactant or a mixture thereof. According to one embodiment, the oil dispersion of the invention comprises at least one non-ionic surfactant. According to one embodiment, the oil dispersion of the invention comprises at least one cationic surfactant. According to one embodiment, the oil dispersion of the invention comprises at least one non-ionic surfactant and at least one cationic surfactant. Preferably, the oil dispersion comprises an amount of surfactant ranging from 0.0001% to 10%, preferably from 0.005 to 5%, more preferably from 0.01% to 2% w/w.

According to one embodiment, non-ionic surfactant may be selected from tyloxapol, poloxamer such as poloxamer 282 or poloxamer 188 or Pluronic F-68LF or Lutrol F68, polysorbate such as polysorbate 20 or polysorbate 80, solutol, polyoxyethylene fatty acid esters such as Emulphor, polyoxyethylene alkyl ethers, polyoxyethylene castor oil derivatives such as Cremophor EL or Cremophor RH, polyoxyethylene sorbitan fatty acid esters, polyoxyethylene stearates, sodium lauryl sulfate, sorbitan esters, vitamin E derivatives such as vitamin E-TPGS (tocopheryl polyethylene glycol succinate) or a mixture thereof. According to one embodiment, the non-ionic surfactant is selected from polysorbate, preferably polysorbate 80; tyloxapol; poloxamer, preferably poloxamer 188; a mixture of poloxamer and tyloxapol; vitamin E derivatives, preferably vitamin E-TPGS; Cremophor RH, preferably Cremophor RH40.

According to one embodiment, anionic surfactant may be selected from anionic phospholipids such as lecithins, docusate sodium, emulsifying wax BP, sodium lauryl sulfate or a mixture thereof.

According to one embodiment, cationic surfactant may be selected from cetalkonium chloride (CKC), benzethonium chloride, cetrimide, cationic lipids, oleylamine, stearylamine, DOTAP (N-[1-(2,3-dioleoyloxy) propyl]-N,N,N trimethylammonium) chloride, DOPE (dioleoyl phosphatidylethanolamine), poly(ethylenimine) (PEI), poly-L-lysine (PLL) or a mixture thereof. According to a specific embodiment, the cationic surfactant is cetalkonium chloride (CKC) or cetrimide, more preferably CKC.

According to one embodiment, especially when the oil dispersion is a cationic emulsion, the dispersion comprises at least one cationic surfactant. Preferably, cationic oil dispersion comprises an amount of cationic surfactant ranging from 0.0001% to 2%, preferably from 0.001% to 1%, more preferably from 0.002% to 0.5% w/w.

According to one embodiment, the cationic surfactant is not a preservative agent. In the case where the surfactant may have a preservative activity, the surfactant is used in the oil dispersion of the invention in an amount inferior to a preservative effective amount. According to a specific embodiment, when the cationic surfactant is cetalkonium chloride (CKC), it is used in the oil dispersion of the invention at a concentration at which CKC does not have any preservative activity.

According to one embodiment, the oil dispersion of the invention further comprises additives such as antioxidants, osmotic agents, viscosifying agents, pH adjusters, buffering agents, solubilizers, chelating agents or thickener agents.

According to one embodiment, osmotic agent may be glycerol, mannitol, sorbitol, sodium chloride or a mixture thereof. Preferably, the oil dispersion comprises an amount of osmotic agent which provides an osmolality comprised between 180 mosm/kg and 300 mosm/kg to the oil dispersion. According to one embodiment, the osmolality is measured by freezing point depression technic, preferably using a Roebling Type 13 osmometer (Berlin, Germany).

According to one embodiment, antioxydants may be alpha-tocopherol, sodium bisulfite, sodium metasulfite, sodium thiosulfate anhydrous, citric acid monohydrate, ascorbyl palmitate or ascorbic acid.

According to an embodiment, the buffering agent may be citrate, phosphate, tris, acetate, carbonate, histidine, gluconate, lactate, trometamine or a mixture thereof. In one embodiment, the buffering agent is not boric acid.

According to one embodiment, the pH of the aqueous phase of the oil dispersion of the invention is preferably ranging from 4.5 to 7.5, more preferably from 5 to 7.

In one embodiment, the oil dispersion of the invention is useful for eye care or for the treatment of eye diseases or eye conditions. In a preferred embodiment, eye diseases or eye conditions are dry eye condition such as dry-eye syndrome or chronic dry-eye diseases such as keratoconjunctivis sicca (KCS), atopic keratoconjunctivitis (AKC) and vernal keratoconjunctivitis (VKC), glaucoma, ocular inflammation conditions such as keratitis, corneal epithelium erosion, uveitis, intraocular inflammation, allergy and dry-eye syndrome ocular infections, ocular infections, ocular allergies, corneal or conjunctival lesions, cancerous growth, neovessel growth originating from the cornea, retinal edema, macular edema, diabetic retinopathy, retinopathy of prematurity, degenerative diseases of the retina (macular degeneration, retinal dystrophies), retinal diseases associated with glial proliferation, anesthesia of the cornea, mydriase of the pupil.

The oil dispersion of the present invention is particularly well suitable for long term treatment of eye diseases or eye conditions, especially for patient that are intolerant to conventional preservative agents. By long-term treatment is meant a treatment exceeding 15 days, or a treatment exceeding 30 days.

According to one embodiment, the oil dispersion of the invention further comprises a therapeutically active agent. Preferably, the therapeutically active agent is hydrophobic and is within the oily phase of the dispersion. In one embodiment, the active agent is selected from antiallergenics such as sodium cromoglycate, antazoline, methapyriline, chlorpheniramine, cetirizine, olapatadine, ketotifen, azelastine, epinastine, emedastine, levocabastive, terfenadine, astemizole and loratadine, pyrilamine or prophenpyridamine; synthetic glucocorticoids and mineralocorticoids and more generally hormones forms derivating from the cholesterol metabolism (progesterone, estrogens, androgenic hormones such as testosterone DHEA and their derivatives); anti-inflammatories such as cortisone, hydrocortisone, hydrocortisone acetate, dexamethasone, dexamethasone 21-phosphate, fluorocinolone, medrysone, prednisone, methylprednisone, prednisolone acetate, fluoromethalone, triamcinolone, betamethasone, loteprednol, flumethasone, mometasone, danazol, beclomethasone, difluprednate and triamcinolone acetonide and their derivatives; non-steroidal anti-inflammatories such as salicylate, indomethacin, ibuprofen, diclofenac, flurbiprofen, 2-arylpropionic acids, N-arylanthranilic acids, oxicams, sulphonanilides, pyrazolidines derivatives, arylalkanoic acids, 3-benzolphenylacetic acids and derivatives, piroxicam and COX2 inhibitors such as rofecoxib, diclofenac, nimesulide, nepafenac; antineoplastics such as carmustine, cisplatin, mitomycin and fluorouracil; immunological drugs such as vaccines and immune stimulants; insulin, calcitonin, parathyroid hormone and peptide and vasopressin hypothalamus releasing factor; beta adrenergic blockers such as timolol maleate, levobunolol HCl and betaxolol HCl, timolol-base, betaxolol, atenolol, befundol, metipranolol, forskolin, cartrolol, epinephrine, dipivalyl, oxonolol, acetazolamide-base and methazolamide; cytokines, interleukins, prostaglandins (also antiprostaglandins, and prostaglandin precursors) such as latanoprost, bimatoprost, tafluprost or travoprost, and growth factors (growth factors such as epidermal growth factor, fibroblast growth factor, platelet derived growth factor, transforming growth factor beta, ciliary neurotrophic growth factor, glial derived neurotrophic factor, NGF, EPO, PlGF); anti-angiogenic compounds such as VEGF inhibitors, VEGF soluble receptors, VEGF-traps, VEGF-antibodies, VEGF-traps, anti VEGF-siRNA; antibodies or antibodies fragments, oligoaptamers, aptamers and gene fragments (oligonucleotides, plasmids, ribozymes, small interference RNA, nucleic acid fragments, peptides, antisense sequences); immunomodulators such as natural or synthetic cyclosporines, endoxan, sirolimus, tacrolimus, thalidomide, tamoxifene; secretagogues such as pilocarpine or celameline; mucin secretagogues such as 15(S)-HETE, ecabet or diquafosol; antithrombolytic and vasodilator agents such as rtPA, urokinase, plasmin, nitric oxide donors; androgen mimetics, flaxseed oil supplements, agonists of adenosine A3 receptor, squalene; antioxidants such as lutein, vitamins, especially vitamin A; inhibitors of carbonic anhydrase such as brinzolamide, dorzolamide, acetazolamide, methazolamide, dichlorophenamide; sympathomimetics such as brimonidine, apraclonidine, dipivefrine, epinephrine; parasympathomimetics such as pilocarpine; cholinesterase inhibitors such as physostigmine, echothiophate; antivirals, such as idoxuridine, trifluorotymidine, acyclovir, valaciclovir, ganciclovir, cidofovir and interferon; antibiotics such as aminoglycosides, carbacephem, carbapenems, cephalosporins, glycopeptides, penicillins, polypeptides, quinolones, sulfonamides, tetracyclines, chlortetracycline, bacitracin, neomycin, polymyxin, gramicidin, cephalexin, oxytetracycline, chloramphenicol, kanamycin, rifampicin, tobramycin, gentamycin, ciprofloxacin, aminosides, erythromycin, ceftazidime, vancomycine, imipeneme; antifungals such as polyene antibiotics, azole derivatives, imidazole, triazole, allylamines, amphotericin B and miconazole; antibacterials such as sulfonamides, sulfadiazine, sulfacetamide, sulfamethizole and sulfisoxazole, nitrofurazone and sodium propionate; and/or their derivatives; and/or their prodrugs; and/or their precursors; and/or acceptable salts thereof; alone or in combination.

Preferably, the oil dispersion of the invention comprises an amount of active agent ranging from 0.0001% to 5%, preferably from 0.001% to 3%, more preferably from 0.003% to 2% w/w.

According to a specific embodiment, the therapeutically active agent is a prostaglandin, preferably latanoprost, bimatoprost, tafluprost, travoprost or a mixture thereof. In this embodiment, the oil dispersion of the invention comprises an amount of active agent ranging from 0.0001% to 0.1%, preferably from 0.001% to 0.01%, more preferably from 0.003% to 0.007% w/w.

According to another specific embodiment, the therapeutically active agent is an immunomodulator, preferably a cyclosporine such as cyclosporin A, sirolimus, tacrolimus or a mixture thereof. In this embodiment, the oil dispersion of the invention comprises an amount of active agent ranging from 0.001% to 0.5%, preferably from 0.004% to 0.2%, more preferably from 0.05% to 0.1% w/w.

The oil dispersion according to the invention may be administered topically, e.g. to the surface of the eye, especially on cornea or conjunctiva, of a patient.

According to an embodiment, the oil dispersion of the invention is sterilized for example by heat, such as by autoclaving, or by filtration or by irradiation or by gas sterilization.

According to an embodiment, the oil dispersion of the invention is packaged in multi-dose containers.

This invention also relates to a multi-dose container including the oil dispersion of the invention.

In one embodiment, an opened container including the self-preserved oil dispersion of the invention has a shelf-life of a period of time ranging from 15 to 60 days, preferably from 20 to 30 days, more preferably during 28 days.

The invention also relates to a process for manufacturing the oil dispersion of the invention comprising the steps of emulsifying/mixing the oil phase with an aqueous phase comprising boric acid and with at least one suitable surfactant, wherein the optionally active agent is dissolved in the oil phase. The emulsification may be achieved for example by shear mixing.

Another object of this invention is a pre-concentrate of the oil dispersion of the invention and a process for manufacturing said pre-concentrate. According to this invention, a pre-concentrate is defined as an oil dispersion having an amount of oil higher than the amount of oil of the dispersion administered to a patient. In one embodiment, the amount of oil in the pre-concentrated is of at least 5% w/w of the total weight of the dispersion, preferably of at least 8%, more preferably of at least 10%. In an embodiment, the amount of oil in the pre-concentrated is ranging from 5% to 50%, preferably from 8% to 30%, more preferably from 10% to 20%.

According to one embodiment, the pre-concentrate may be sterilized for example by heat, such as by autoclaving, or by filtration or by irradiation or by gas sterilization.

The invention also relates to a process of manufacturing a pre-concentrate of an oil dispersion of the invention comprising the steps of emulsifying/mixing an oil with an aqueous phase and with surfactant, wherein the optionally active agent is dissolved in the oil phase.

The invention also relates to a process of manufacturing the oil dispersion of the invention comprising (1) manufacturing a pre-concentrate as described above and then (2) diluting one volume of the resulting pre-concentrate with 2 to 50 volumes of water or aqueous phase. Boric acid may be present in the aqueous phase used for the manufacturing of the pre-concentrate and/or in the diluting aqueous phase.

According to one embodiment, the emulsification is such that the droplet size or the distribution of the droplet size in the pre-concentrate is about the same as in the final oil dispersion.

According to an embodiment, the diluting water may comprise additives selected from osmotic agents, viscosifying agents, buffering agent, antioxidants or colorants.

According to one embodiment, the self-preserved oil dispersion of the invention is free of conventional preservative agents.

According to a specific embodiment, the self-preserved oil dispersion of the invention if free of benzalkonium chloride, cetrimide, benzethonium chloride or other irritant preservative agents. According to a specific embodiment, the oil dispersion of the invention is free of oxy-chloro components.

According to a specific embodiment, the oil dispersion of the invention is free of zinc.

According to a specific embodiment, the oil dispersion of the invention is free of biocides, especially of biguanide salts.

According to a specific embodiment, the oil dispersion of the invention is free of complexes of borate and amino alcohols. According to a specific embodiment, the oil dispersion of the invention is free of borate-polyols complexes.

According to a specific embodiment, the oil dispersion of the invention is free of zinc and of complexes of borate and amino alcohols. According to a specific embodiment, the oil dispersion of the invention is free of zinc and of borate-polyols complexes.

According to a specific embodiment, the oil dispersion of the invention is free of propylene glycol.

According to a specific embodiment, the oil dispersion of the invention is free of tobramycin. According to a specific embodiment, the oil dispersion of the invention is free of antibiotics.

According to a specific embodiment, the oil dispersion of the invention is free of sodium hyaluronate.

According to a specific embodiment, the oil dispersion of the invention is free of sorbic acid. According to a specific embodiment, the oil dispersion of the invention is free of sodium edetate. According to a specific embodiment, the oil dispersion of the invention is free of sodium edetate and free of sorbic acid.

According to a specific embodiment, the oil dispersion of the invention is free of polymeric quaternary ammonium compounds.

According to a specific embodiment, the oil dispersion of the invention is free of hydroxyalkyl cellulosic polymer and/or polyalkylene glycol.

According to a specific embodiment, the oil dispersion of the invention is free of phospholipids. According to a specific embodiment, the oil dispersion of the invention is free of mucoadhesive polymers.

In the present invention, boric acid is not a buffering agent. Especially, boric acid is not used as a member of a pH damper system such as a boric acid/borate system nor at a concentration able to provide a buffering effect to the composition of the invention.

EXAMPLES

The present invention is further illustrated by the following examples.

Example 1: Self-Preserved Oil-in-Water Emulsions

Emulsion 1

| Ingredient | Function | % w/w |
| --- | --- | --- |
| Boric acid | preservation promoter | 0.02% |
| MCT | oil | 1% |
| Latanoprost | active agent | 0.005% |
| Cetalkonium chloride | cationic surfactant | 0.005% |
| Polysorbate 80 | non-ionic surfactant | 0.05% |
| Glycerol | osmotic agent | 2.4% |
| Water | vehicle | QS 100% |

Emulsion 2

| Ingredient | Function | % w/w |
| --- | --- | --- |
| Boric acid | preservation promoter | 0.02% |
| MCT | oil | 1% |
| Tafluprost | active agent | 0.0015% |
| Cetalkonium chloride | cationic surfactant | 0.005% |
| Polysorbate 80 | non-ionic surfactant | 0.05% |
| Glycerol | osmotic agent | 2.4% |
| Water | vehicle | QS 100% |

Emulsion 3

| Ingredient | Function | % w/w |
| --- | --- | --- |
| Boric acid | preservation promoter | 0.02% |
| MCT | oil | 1% |
| Cyclosporin A | active agent | 0.1% |
| Cetalkonium chloride | cationic surfactant | 0.005% |
| Tyloxapol | non-ionic surfactant | 0.3% |
| Poloxamer 188 | non-ionic surfactant | 0.1% |
| Glycerol | osmotic agent | 2.4% |
| Water | vehicle | QS 100% |

Emulsion 4

| Ingredient | Function | % w/w |
| --- | --- | --- |
| Boric acid | preservation promoter | 0.01% |
| mineral oil light | Oil | 0.5% |
| mineral oil heavy | Oil | 0.5% |
| Cetalkonium chloride | cationic surfactant | 0.002% |
| Tyloxapol | non-ionic surfactant | 0.3% |
| Poloxamer 188 | non-ionic surfactant | 0.1% |
| Tris Hydrochloride | buffer | 0.071% |
| tromethamine | buffer | 0.006% |
| Glycerol | osmotic agent | 1.2% |
| Water | vehicle | QS 100% |

Emulsion 5

| Ingredient | Function | % w/w |
| --- | --- | --- |
| Tricopper diborate | preservation promoter | 0.01% |
| MCT | oil | 1% |
| Sirolimus | active agent | 0.01% |
| Cetalkonium chloride | cationic surfactant | 0.005% |
| Tyloxapol | non-ionic surfactant | 0.3% |
| Poloxamer 188 | non-ionic surfactant | 0.1% |
| Glycerol | osmotic agent | 2.4% |
| Water | vehicle | QS 100% |

Emulsion 6

| Ingredient | Function | % w/w |
| --- | --- | --- |
| Borax | preservation promoter | 0.015% |
| MCT | oil | 10% |
| Dexamethasone base | active agent | 0.8% |
| Cetrimide | cationic surfactant | 0.009% |
| Vitamine E TPGS | non-ionic surfactant | 5.0% |
| Mannitol | osmotic agent | 5% |
| Water | vehicle | QS 100% |

Process of Manufacturing of the Emulsions:

The oily phase components (oil and active agent) were successively weighted in the same beaker and then magnetically stirred under a slight heating (40° C.). Aqueous phase components (boric acid, surfactants, tonicity agents, buffer) were successively weighted in the same beaker and then magnetically stirred under a slight heating (40° C.). Both phases were heated to 65° C. An emulsion was formed by rapid addition of the aqueous phase in the oily phase and was then rapidly heated to 75° C. The emulsion droplet size was then decreased by a 5 minutes high shear mixing with POLYTRON PT 6100. The emulsion became milky. The emulsion temperature was cooled down to 20° C. using an ice bath. The final emulsion was obtained by homogenization on a microfluidizer (C5, Avestin) using continuous cycles for 5 min at a pressure of 10 000 psi. The emulsion temperature was decreased to 25° C. Its pH was measured and then adjusted to 8.00 using a 0.1 M HCl or 0.1M NaOH solution. Emulsion was conditioned in glass vial with nitrogen bubbling and then sterilized in an autoclave 20 min at 121° C.

The mean particle size was determined by quasi-elastic light scattering after dilution in water using a High Performance Particle Sizer (Malvern Instruments, UK). The electrophoretic mobility was measured at 25° C. in a Malvern Zetasizer 2000 (Malvern Instruments, UK) following a 1:200 dilution in double distilled water. The value of electrophoretic mobility allowed calculating zeta potential, as electrophoretic mobility and zeta potential are related to by the Henry equation. The osmolality was measured by freezing point depression technic, using a Roebling osmometer.

TABLE 1

Physicochemical characterization of emulsions 1-6 of example 1

| Emulsion number | Aspect after sterilization Visual | Zeta potential (mV) | Osmolality (mOsm/kg) | pH | Droplet size (nm) |
| --- | --- | --- | --- | --- | --- |
| Emulsion 1 | Good | +35 | 290 | 6.1 | 250 |
| Emulsion 2 | Good | +33 | 300 | 5.5 | 230 |
| Emulsion 3 | Good | +35 | 285 | 5.8 | 280 |
| Emulsion 4 | Good | +38 | 160 | 5.47 | 192 |

TABLE 1-continued

Physicochemical characterization of emulsions 1-6 of example 1

| Emulsion number | Aspect after sterilization Visual | Zeta potential (mV) | Osmolality (mOsm/kg) | pH | Droplet size (nm) |
|---|---|---|---|---|---|
| Emulsion 5 | Good | +30 | 305 | 6.3 | 180 |
| Emulsion 6 | Good | +25 | 300 | 7.0 | 405 |

Example 2: Preservation Efficacy Test

Emulsions 1-6 of example 1 were submitted to preservation efficacy tests according to European Pharmacopoeia (7$^{th}$ edition, monograph 5.1.3.). Emulsions 1'-6', identical to emulsions 1-6 of example 1, but deprived of boric acid, were also tested for comparison.

Briefly, these tests consist in the introduction of microorganism in the emulsion and to follow the growth or decrease over 28 days (*pseudomonas aeruginosa, staphylococcus aureus, candida albicans, aspergillus brasiliensis*). Results are presented in Table 2 below.

TABLE 2

Emulsions 1-6 of example 1 and corresponding free of boric acid emulsions tested for antimicrobial efficacy against European pharmacopeias test.

| Emulsion number | European Pharmacopeia |
|---|---|
| Emulsion 1 | Meet test |
| Emulsion 1' (without boric acid) | Test not met |
| Emulsion 2 | Meet test |
| Emulsion 2' (without boric acid) | Test not met |
| Emulsion 3 | Meet test |
| Emulsion 3' (without boric acid) | Test not met |
| Emulsion 4 | Meet test |
| Emulsion 4' (without boric acid) | Test not met |
| Emulsion 5 | Meet test |
| Emulsion 5' (without boric acid) | Test not met |
| Emulsion 6 | Meet test |
| Emulsion 6' (without borax) | Test not met |

Example 3: Effect of the Concentration on Preservation Efficacy

Emulsion 1

| Ingredient | Function | % w/w |
|---|---|---|
| Boric acid | preservation promoter | Varying concentration |
| MCT | oil | 1% |
| Latanoprost | active agent | 0.005% |
| Cetalkonium chloride | cationic surfactant | 0.005% |
| Polysorbate 80 | non-ionic surfactant | 0.05% |
| Glycerol | osmotic agent | 2.4% |
| Water | vehicle | QS 100% |

Emulsions based on emulsion 1 of example 1 are manufactured using borax or tricopper diborate as preservation promoter in varying concentrations. Antimicrobial efficacy is evaluated against European Pharmacopeia test 5.1.3 as in example 2. Results are presented in table 3 below.

TABLE 3

Antimicrobial efficacy against European pharmacopeias test of emulsions comprising varying concentrations of borax or tricopper diborate as preservation promoters.

| | Concentration | | | | | |
|---|---|---|---|---|---|---|
| | 0.0001% | 0.001% | 0.005% | 0.01% | 0.02% | 0.05% |
| Borax | Test not met | Test not met | Meet test | Meet test | Meet test | Meet test |
| Tricopper diborate | Test not met | N/A | Meet test | Meet test | Meet test | Meet test |

Example 4: In Vivo Evaluation

This example aims at evaluating the ocular tolerance of cationic emulsions containing boric acid or tricopper diborate of example 1 in an in vivo rabbit model.

The test was performed using the model published by Liang et al. Molecular Vision, 2008, 14, 204-216, which was developed to evaluate the ocular tolerance of cationic oil-in-water emulsion. The ocular tissues alterations observed following the 15 instillations mimicking those observed following long term daily treatment with ocular eye drops, it was of particular interest to evaluate the ocular tolerance of the self-preserved preserved emulsions of the invention. Published data for the unpreserved cationic emulsion of latanoprost were used as comparator and demonstrate the good tolerance and safety of this unpreserved version of the emulsion.

The table below summarizes the data obtained for 5 emulsions described in example 1.

| | IVCM scores | | | Inflammatory cells |
|---|---|---|---|---|
| Emulsion | Min 75 | Hour 4 | Day 1 | in the CALT |
| Emulsion 1 | ++ | +++ | +++ | +++ |
| Emulsion 3 | +++ | +++ | +++ | +++ |
| Emulsion 4 | +++ | +++ | +++ | ++ |
| Emulsion 5 | + | ++ | ++ | ++ |
| Emulsion 6 | + | + | ++ | + |
| Unpreserved emulsion (Ctl) Liang et al. Molecular Vision, 2009, 15, 1690-1699 | +++ | +++ | +++ | +++ |

IVCM: in vivo confocal microscopy. Calculations of the scores are described in Liang et al. Molecular Vision, 2008, 14, 204-216 and Liang et al. Molecular Vision, 2009, 15, 1690-1699. Scores below 2 indicates that the eye drop induced minimal changes and is representative of a well-tolerated eye drop. Definition of the scale used in the table: +++, score < 1; ++, 1 < score < 2; +, <2score < 3; −, 3 < score < 5.
CALT: conjunctival associated lymphoid tissue. The lower the inflammatory the cell counts, the better the tolerance. Cell count < 100, +++; 100 < cell count < 500, ++; 500 < cell count < 1000, +; cell count > 1000, −.

In conclusion, the 5 tested emulsions of the invention are well tolerated by the rabbit ocular surface.

The invention claimed is:

1. A cationic oil dispersion comprising a dispersed oil phase, an aqueous phase, at least one cationic surfactant, and boric acid or a salt thereof, the boric acid present in an amount ranging from 0.005% to 0.075% by weight of the total weight of the cationic oil dispersion, wherein said amount of boric acid is effective to self-preserve the cationic oil dispersion and wherein the cationic oil dispersion does not contain conventional preservative agents and does not contain sorbic acid.

2. The cationic oil dispersion of claim 1, having sufficient preservative activity to comply with USP and/or Ph. Eur. preservative efficacy requirements.

3. The cationic oil dispersion of claim 1, wherein the dispersion is an oil-in-water emulsion.

4. The cationic oil dispersion of claim 1, wherein the amount of boric acid ranges from 0.008 to 0.05% w/w.

5. The cationic oil dispersion of claim 1, wherein the amount of boric acid ranges from 0.01 to 0.05% w/w.

6. The cationic oil dispersion of claim 1, wherein the amount of boric acid ranges from 0.01 to 0.02% w/w.

7. The cationic oil dispersion of claim 1, wherein the boric acid is sodium borate, sodium metaborate, calcium borate, borax, tricopper diborate, trioleyl borate, lithium borate, tris(trimethylsilyl) borate, ethyl borate, potassium tetrafluoroborate, disodium dihydrogen borate, manganese borate, oleyl borate, tripentyl borate, tributyl borate, trimethyl borate, tridodecyl borate, triazanium borate, or a combination of any of the foregoing.

8. The cationic oil dispersion of claim 1, wherein the oil phase comprises an oil selected from mineral oil, medium chain triglycerides), triglyceride oils, vegetable oils, corn oil, olive oil, soybean oil, sesame oil, cotton seed oil, sweet almond oil, fatty acid, isopropyl myristate, oily fatty alcohols, esters of sorbitol and fatty acids, oily sucrose esters, and a combination of any of the foregoing.

9. The cationic oil dispersion of claim 1, wherein the cationic surfactant is selected from cetalkonium chloride (CKC), benzethonium chloride, cetrimide, cationic lipids, oleylamine, stearylamine, DOTAP (N-[1-(2,3-dioleoyloxy)propyl]-N,N,N trimethylammonium) chloride, DOPE (dioleoyl phosphatidylethanolamine), poly(ethylenimine) (PEI), poly-L-lysine (PLL), and a combination of any of the foregoing.

10. The cationic oil dispersion of claim 1, comprising a non-ionic surfactant.

11. The cationic oil dispersion of claim 10, wherein the non-ionic surfactant is selected from tyloxapol, poloxamer, polysorbate, solutol, polyoxyethylene fatty acid esters, polyoxyethylene castor oil derivatives, polyoxyethylene sorbitan fatty acid esters, polyoxyethylene stearates, sodium lauryl sulfate, sorbitan esters, vitamin E derivatives, and a combination of any of the foregoing.

12. The cationic oil dispersion of claim 1, further comprising a therapeutically active agent.

13. The cationic oil dispersion of claim 12, wherein the therapeutically active agent is selected from antiallergenics; synthetic glucocorticoids and mineralocorticoids; hormones derived from progesterone, estrogens, or androgenic hormones; anti-inflammatories; non-steroidal anti-inflammatories; immunological drugs; insulin, calcitonin, parathyroid hormone and peptide and vasopressin hypothalamus releasing factor; beta adrenergic blockers; prostaglandins; growth factors; anti-angiogenic compounds; antibodies, antibody fragments, oligoaptamers, aptamers, gene fragments, oligonucleotides, plasmids, ribozymes, small interference RNA, nucleic acid fragments, peptides, antisense sequences; immunomodulators; secretagogues; mucin secretagogues; antithrombolytic and vasodilator agents; androgen mimetics, flaxseed oil supplements, agonists of adenosine A3 receptor, squalene; antioxidants; inhibitors of carbonic anhydrase; sympathomimetics; parasympathomimetics; cholinesterase inhibitors; antivirals; antibiotics; antifungals; antibacterials; derivatives of any of the foregoing; prodrugs of any of the foregoing; precursors of any of the foregoing; acceptable salts of any of the foregoing; and a combination of any of the foregoing.

14. The cationic oil dispersion of claim 12, wherein the therapeutically active agent is selected from cortisone, hydrocortisone, hydrocortisone acetate, dexamethasone, dexamethasone 21-phosphate, fluorocinolone, medrysone, prednisone, methylprednisone, prednisolone acetate, fluoromethalone, triamcinolone, betamethasone, loteprednol, flumethasone, mometasone, danazol, beclomethasone, difluprednate and triamcinolone acetonide and their derivatives; latanoprost, bimatoprost, tafluprost or travoprost; natural or synthetic cyclosporines, endoxan, sirolimus, tacrolimus, thalidomide, and tamoxifene.

* * * * *